(12) United States Patent
Allen et al.

(10) Patent No.: US 9,005,669 B2
(45) Date of Patent: Apr. 14, 2015

(54) SYNERGY OF STRONG ACIDS AND PEROXY COMPOUNDS

(75) Inventors: Randall R. Allen, Shreveport, LA (US); James Knocke, Cleveland, TN (US); Carleton J. Parker, III, Fort Worth, TX (US); Jason York, Olive Branch, MS (US); Dean T. Didato, Germantown, TN (US)

(73) Assignee: Synergy Technologies, Inc., Shreveport, LA (US)

( * ) Notice: Subject to any disclaimer, the term of this patent is extended or adjusted under 35 U.S.C. 154(b) by 37 days.

(21) Appl. No.: 13/285,341

(22) Filed: Oct. 31, 2011

(65) Prior Publication Data

US 2012/0052133 A1    Mar. 1, 2012

Related U.S. Application Data

(63) Continuation of application No. 13/100,862, filed on May 4, 2011, now abandoned.

(60) Provisional application No. 61/331,448, filed on May 5, 2010.

(51) Int. Cl.

| | | |
|---|---|---|
| *A01N 59/00* | (2006.01) | |
| *A01P 1/00* | (2006.01) | |
| *A01N 37/02* | (2006.01) | |
| *A23B 7/157* | (2006.01) | |
| *A01N 37/16* | (2006.01) | |
| *A23B 4/20* | (2006.01) | |
| *A23B 4/24* | (2006.01) | |
| *A23B 7/154* | (2006.01) | |
| *A23L 3/3508* | (2006.01) | |
| *A23L 3/358* | (2006.01) | |

(52) U.S. Cl.
CPC ............... *A23B 7/157* (2013.01); *A01N 37/16* (2013.01); *A23B 4/20* (2013.01); *A23B 4/24* (2013.01); *A23B 7/154* (2013.01); *A23L 3/3508* (2013.01); *A23L 3/358* (2013.01)

(58) Field of Classification Search
USPC .......................................................... 424/616
See application file for complete search history.

(56) References Cited

U.S. PATENT DOCUMENTS

| | | |
|---|---|---|
| 4,172,086 A | 10/1979 | Berkowitz |
| 4,915,955 A | 4/1990 | Gomori |

(Continued)

FOREIGN PATENT DOCUMENTS

EP    0 618 612 A2    3/1994

OTHER PUBLICATIONS

Stoker, H. Steven; General, Organic and Biological Chemistry, 2007, Houghton Mifflin, p. 254.*

(Continued)

*Primary Examiner* — Mina Haghighatian
*Assistant Examiner* — Erin Hirt
(74) *Attorney, Agent, or Firm* — Stites & Harbison PLLC; Cong Ding

(57) ABSTRACT

Disclosed is a method for improving decontamination in meat, poultry, fish, fruit and vegetable processing using a combination of acid(s) and peroxy compound(s). The method comprises a "stacked" approach, sequentially adding the acid(s) and peroxy compound(s) to an aqueous stream to provide a point-of-use low-pH antimicrobial composition that is highly effective for decontamination of food products, as well as safer for use in a processing facility.

15 Claims, 3 Drawing Sheets

(56) References Cited

U.S. PATENT DOCUMENTS

| | | |
|---|---|---|
| 5,122,538 A | 6/1992 | Lokkemoe et al. |
| 5,200,189 A | 4/1993 | Oakes et al. |
| 5,294,570 A | 3/1994 | Fleming, Jr. et al. |
| 5,632,676 A | 5/1997 | Kurschner et al. |
| 6,010,729 A | 1/2000 | Gutzmann et al. |
| 6,103,286 A | 8/2000 | Gutzmann et al. |
| 6,113,963 A | 9/2000 | Gutzmann et al. |
| 6,183,807 B1* | 2/2001 | Gutzmann et al. ............ 426/652 |
| 6,319,888 B2* | 11/2001 | Wei et al. ...................... 510/441 |
| 6,375,976 B1 | 4/2002 | Roden et al. |
| 7,510,721 B2 | 3/2009 | Roden et al. |
| 2009/0043123 A1* | 2/2009 | Copenhafer et al. .............. 562/6 |
| 2009/0081311 A1* | 3/2009 | Man et al. ...................... 424/616 |

OTHER PUBLICATIONS

Senese, F. "Why does mixing a strong acid with water release so much heat?" Oct. 12, 1999 http://web.archive.org/web/19991012001728/http://antoine.frostburg.edu/chem/senese/101/thermo/faq/always-add-acid.shtml.*

Gagnaire, Marignac, Hecht and Hery, Sensory Irritation of Acetic Acid, Hydrogen Peroxide, Peroxyacetic Acid and their Mixture in Mice, 2002, pp. 97-102.

* cited by examiner

SYNERGY OF STRONG ACIDS AND PEROXY COMPOUNDS

This application is a continuation application of U.S. patent application Ser. No. 13/100,862 filed May 4, 2011, now abandoned, which claims priority to U.S. Patent Application No. 61/331,448, filed May 5, 2010. All of the prior applications are incorporated herein by reference in their entirety.

FIELD OF THE INVENTION

The invention relates to chemical sanitizing and/or disinfecting methods. More specifically, the invention relates to methods for reducing microbial contamination in food products.

BACKGROUND OF THE INVENTION

All poultry carcasses entering the processing environment are contaminated with bacteria, some with pathogenic bacteria such as pathogenic *Salmonella* species. Fecal matter and dirt are the main sources of this contamination. *Campylobacter* infection from poultry sickens more than 600,000 people per year in the United States alone. *Salmonella*-associated illness is the most commonly diagnosed and reported foodborne illness, with 19,336 individuals hospitalized with the infection in 2010 in the United States, and 378 deaths in the U.S. alone.

Poultry is typically washed at any of several steps during the process of converting a live bird to an edible food product. Decontamination is more difficult because many types of bacteria are able to adhere within only 15 seconds of contact and a significant number of carcasses can become cross-contaminated with pathogens during handling, scalding, mechanical processing, and chilling. Water used for washing or other procedures is often used repeatedly over time, which provides yet another opportunity spreading, rather than reducing, microbial burden on poultry.

Microbial contamination or cross contamination of poultry via water continues to be a major concern for poultry processors and end users. Although washing, cooling, or heating poultry carcasses with water can reduce potential contamination, the processing water can also serve as a source of contamination or cross contamination. If pathogenic microorganisms in water are not removed, inactivated or otherwise controlled, they can spread to other poultry, potentially contaminating them. Handling or processing steps that pool many individual poultry parts also tend to increase the risk that a single contaminated item may contaminate the entire lot.

A variety of chemical means exist for reducing microbial contamination in processing and fabrication of meat and poultry. However, there still exists a need for more effective compositions to reduce the bacterial load and minimize the risk of food-borne illness.

SUMMARY OF THE INVENTION

The present invention relates to a method comprising admixing at least one acid and at least one compound chosen from the group consisting of at least one peroxyacid, at least one peroxygen, and combinations thereof, wherein the admixing comprises a first step of establishing an aqueous stream comprising at least one strong acid and having a pH of from about 0.5 to about 3.5, and a second step of adding into the aqueous stream at least one peroxy compound chosen from the group consisting of peroxyacids, peroxygens, peracetic acid, hydrogen peroxide, and combinations thereof, to form an antimicrobial composition for decontamination of a food product selected from the group consisting of poultry, meat, fish, and vegetables. In various aspects, the first step may comprise establishing an aqueous stream comprising at least one peroxy compound chosen from the group consisting of peroxyacids, peroxygens, and combinations thereof, and a second step of admixing into the aqueous stream at least one strong acid and having a pH of from about 0.5 to about 3.5. In various aspects, the at least one peroxyacid is peroxyacetic acid. The at least one peroxygen may, for example, comprise hydrogen peroxide.

In various aspects of the method, the antimicrobial composition is directed to at least one endpoint selected from the group consisting of a mist, a spray, a dip, a deluge, a flume, an electrostatic application, and atomization, for application of the antimicrobial composition to the food product.

The invention also relates to a composition comprising a concentration of from about 1 (one) to about 40 percent of at least one peroxy compound chosen from the group consisting of peroxyacids, peroxygens, and combinations thereof, and from about 5 to about 35 percent of at least one acid, wherein the at least one acid comprises at least one buffered acid, the composition being effective for reducing bacterial contamination of a food product while being safe for contact with human skin. In various aspects, the at least one peroxyacid may be peroxyacetic acid, and in some aspects of the invention the peroxyacetic comprises less than 100 ppm for when the composition is intended for application to poultry. In other aspects, the peroxyacetic may comprise up to 230 ppm for red meat applications.

DETAILED DESCRIPTION

The inventors have developed a method for increasing decontamination efficiency in meat, poultry, fish, fruit, and/or vegetables, the method comprising separately adding into an aqueous stream at least one acid and at least one peroxy compound chosen from the group consisting of peroxyacids, peroxygens, and combinations thereof, to form an antimicrobial composition which may then be directed to the surface of a poultry product, a meat product, a fish product, or a vegetable product. Peroxy compounds, such as peroxyacids including, for example, peroxyacetic (peracetic) acid (PM), and peroxygens such as, for example, hydrogen peroxide, are commonly used for decontamination, but although they are generally quite effective, it would be beneficial, especially considering the significant health risk that may be associated with residual contamination of meat/poultry products, to improve the effectiveness of peroxy compounds. Compositions have previously been made by mixing strong acids and peroxy compounds, but those compositions have generally been used for cleaning laboratory glassware and as a stripping agent for removing highly cross-linked organic polymer in the semiconductor industry. As one would expect, precautions must be taken with those compositions because they have such potential for damaging animal tissue, especially human skin. The inventors have developed a method that allows these compounds to be admixed to produce a peroxy/acid composition that has improved decontamination efficacy over that of the currently-used standard, PM, while being safe for application to meat, poultry, fish, fruit, and/or vegetables, etc., with the added benefit of being safe for contact with human skin.

Figure 1:
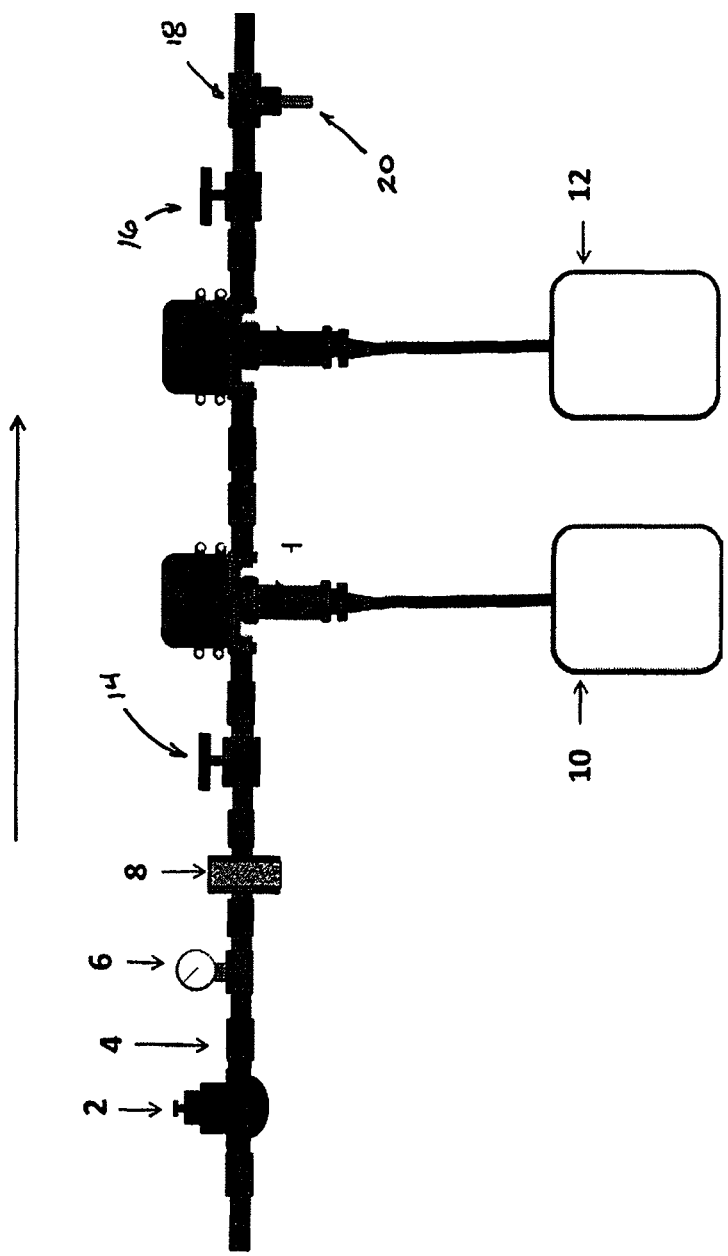
FIG. 1 is a schematic illustrating an apparatus for performing the method of the invention.
Figure 2:
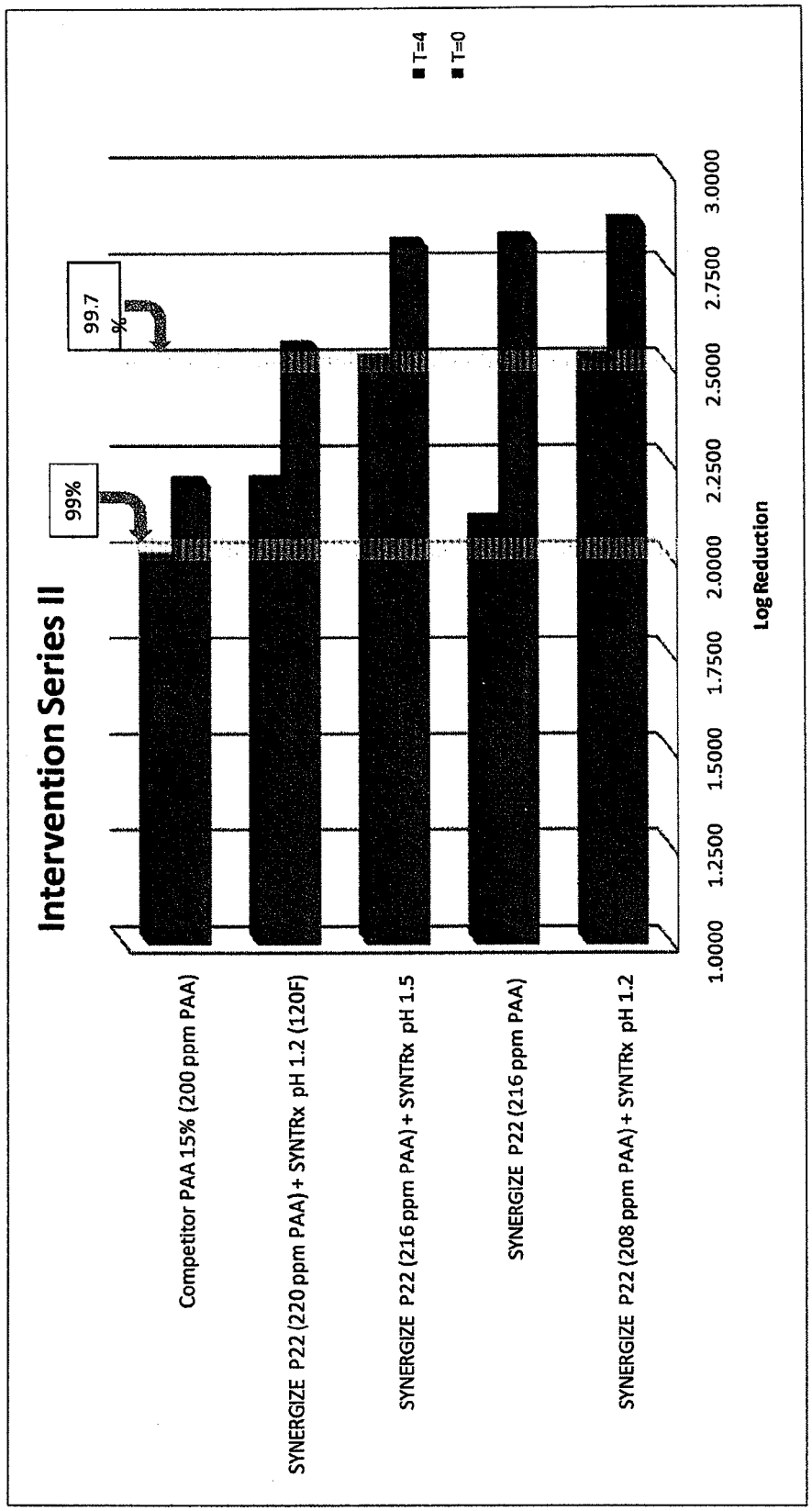
FIG. 2 is a bar graph illustrating the increased efficiencies provided by compositions applied to a red meat product by the method of the invention. For each treatment, indicated along the Y axis, are two horizontal bars. The top horizontal bar of each pair represents results at T=4 and the bottom horizontal bar of each pair represents results at T=0.
Figure 3:
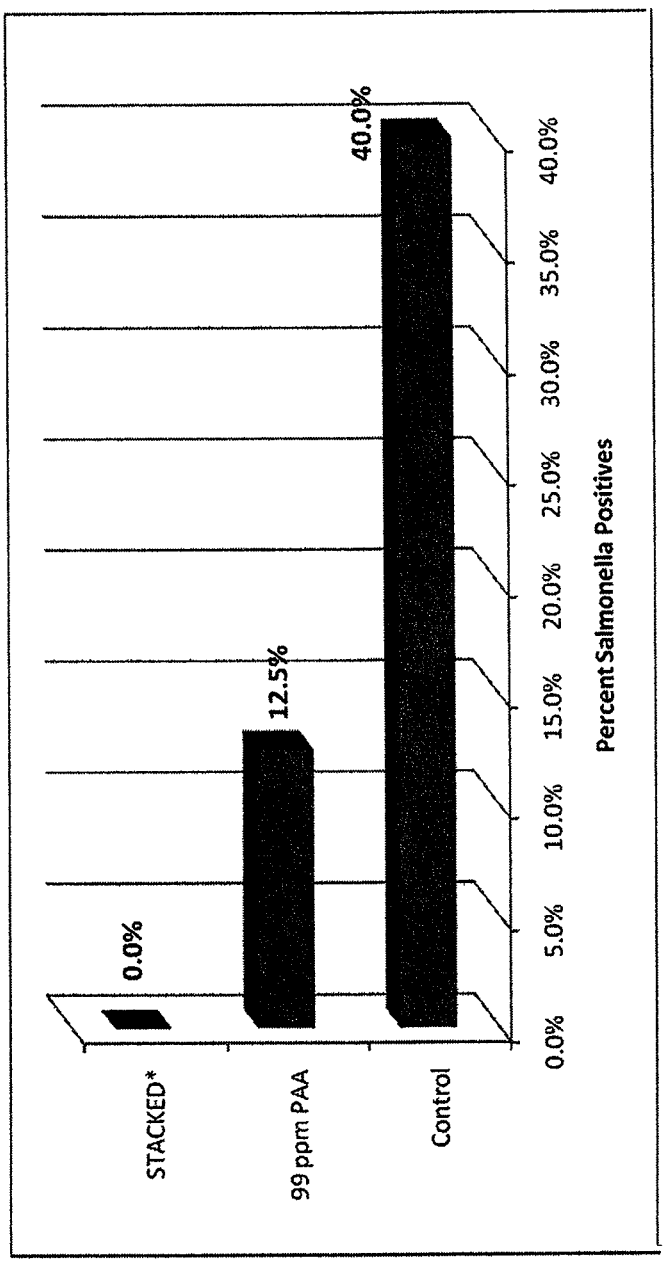
FIG. 3 is a bar graph illustrating the increased efficiency provided by a composition produced by the method of the invention (designated as "Stacked" on the graph), as applied to broiler chickens, where the bars represent the percentage of *Salmonella* sp. positives. Treatments are indicated on the Y axis and percentage of *Salmonella* positives is indicated on the X axis.

In the method of the invention, the introduction of the first component and the second component into an aqueous stream, as shown in FIG. 1, may be performed by adding the acid, followed by adding the peroxy compound, or may be performed by adding the peroxy compound, followed by adding the acid. That is, it is not necessary to add the two components in a particular order, provided that they are introduced into an aqueous stream separately or, alternately, formed from two separate aqueous streams, with the resulting admixed peroxy/strong acid producing an antimicrobial composition having a pH of from about 0.5 to about 3.5. Especially effective compositions are provided at a pH of from about 0.5 to about 3.0. As an example, turning to FIG. 1, there is shown generally an apparatus for admixing a first component and a second component into an aqueous stream within the apparatus, where the flow direction is indicated by the left-to-right arrow. A pressure valve 2 may be used to regulate the flow rate, the pressure valve 2 being fluidly connected to a fluid channel 4, such as a metal pipe, a polymer pipe (PVC, etc.), etc. Pressure within the fluid channel 4 may be monitored by means of a pressure gauge 6, with incoming potable process water being subject to filtration by means of a water filter 8. A first holding tank 10 for concentrated mineral acid, organic acid, or a combination of both, is fluidly connected to the fluid channel 2 so that a predetermined amount of acid may be injected into an aqueous stream formed by the incoming potable process water to produce a desired pH in the aqueous stream. A second holding tank 12 for at least one peroxy compound, such as, for example, concentrated peroxycarboxylic acid and/or hydrogen peroxide, is also fluidly connected to the fluid channel 4 so that the at least one peroxy compound may be added into the aqueous stream, such as by injection, opening/closing of a valve, etc. Shutoff valves 14 and 16 are useful to isolate the holding tanks 10,12 for various operations, and sample port 18 with discharge 20 can be useful for many embodiments. In various aspects of the invention, peroxyacetic acid (PM) may be added from the holding tank into the aqueous stream in the fluid channel to provide a concentration in the aqueous stream of from about 5 ppm to about 230 ppm, for example, and/or hydrogen peroxide may be injected into the aqueous stream from the holding tank to provide a concentration of hydrogen peroxide in the aqueous stream of from about 1 ppm to about 1000 ppm. Using the method of the invention, reagents are admixed sequentially into an aqueous stream which, at its endpoint, produces a ready-to-use antimicrobial composition comprising an aqueous solution of acid/peroxy compound which may be applied to poultry, meat, fish, etc., by means consisting of, for example, a mist, a spray, a dip, a deluge, a flume, an electrostatic application, or atomization.

The inventors have also developed a composition comprising a concentration of from about 1 (one) to about 40 percent of at least one peroxy compound chosen from the group consisting of peroxyacids, peroxygens, and combinations thereof, and from about 5 to about 35 percent of at least one acid, wherein the at least one acid comprises at least one buffered acid ("safe acid"), the composition being effective for reducing bacterial contamination of a food product while being safe for contact with human skin. This provides an advantage both in meat/poultry decontamination and in safety for individuals employed within a processing plant.

As used herein, a "strong acid" is an acid that will achieve the desired pH of from about 0.5 to about 3.5 with the least amount of solids and cost. Examples of strong acids are HCl, $H_2SO_4$, and $H_3PO_4$. However, as used in the method of the invention, a strong acid may include one or more other organic and/or inorganic acids known to those of skill in the art. A "safe acid" is a buffered strong acid that is significantly less corrosive to steel and skin than the strong acid itself. A safe acid may be provided by buffering one or more strong acids using an organic acid, urea, etc. Sulfuric acid, for example, may be buffered by the addition of sodium sulfate. "A compound" includes a mixture of two or more compounds. "Establishing an aqueous stream" is intended to mean producing or establishing a stream comprising water within an apparatus for adding separately into the water at least one peroxy compound and at least one acid, so that an antimicrobial composition comprising water, acid(s), and peroxy compound(s) is formed within the apparatus and may be thereby directed onto the surface of a food product. "Directed onto the surface" refers to contacted with the surface, or the interior, of a food product such as a chicken, for example. This may be accomplished by spraying onto the surface, dipping the bird into the antimicrobial composition, or other means known to those of skill in the art of meat and poultry processing, for example. "Comprising" may also encompass the terms "consisting of" and "consisting essentially of," and ranges recited herein are intended to include sub-ranges thereof. "Chosen from" means chosen from the group consisting of the listed options, and "effective for use in decontamination of poultry; meat, fish, fruit, and vegetables" means effective for decreasing bacterial contamination while maintaining the required integrity of the animal or plant tissue to be used as a food product.

Application of an antimicrobial composition formed by the method of the invention can provide a significant reduction in numbers of a wide variety of microorganisms, such as *Salmonella typhimurium, Campylobacter jejuni, Listeria monocytogenes*, and *Escherichia coli* O157:H7. The method of the present invention may be used to reduce the numbers of a wide variety both Gram positive and Gram negative bacteria, yeast, molds, bacterial spores, viruses, etc. The inventors have found it to be particularly advantageous to utilize the method of the invention wherein the peroxy compound PM and the acid is HCl or $H_2SO_4$. When the HCl or $H_2SO_4$ is buffered, such as by the addition of a weaker acid, the resulting antimicrobial composition is both highly effective against microbes and safe for contact with human skin, making such a composition especially useful in food processing, health, industrial, and institutional settings where decontamination of surfaces should be done with minimal damage or irritation to human or animal tissue. The method of the invention also produces antimicrobial compositions which require the use of lower concentrations of peroxy-containing compound(s), yet produced greater efficacy than compositions having higher concentrations of peroxy-containing compounds, such as those containing higher concentrations of PAA.

The concentration of the two components to be added is dependent on the activity of the peroxyacid, peroxygens, peracetic acid and/or hydrogen peroxide compound and the alkalinity of the fresh potable processing water. The target range for peroxycarboxylic acid is from about 5 ppm to about 230 ppm and the target range for hydrogen peroxide is from about 1 ppm to about 1000 ppm.

The invention can be employed for processing poultry and/or meat, for example, at any step from gathering the live birds through packaging the final product. For example, the present method may be used for washing, rinsing, chilling, or scalding poultry carcasses, poultry carcass parts, or poultry organs for reducing contamination of these items with spoilage/decay-causing bacteria, and pathogenic bacteria.

Before processing, live poultry are generally transported to and gathered at the beginning of a processing line. Poultry can be washed before entering the processing line. A first washing step, known as scalding (e.g. submersion or immersion scalding) loosens attachment of feathers to poultry skin. Submersion scalding typically includes immersing a stunned and bled bird into a scalding hot bath of water or a liquid antimicrobial composition, typically at a temperature of about 50° to about 80° C. A second washing process is generally known as "dress" rinsing, which rinses residual feathers and follicle residues from the carcass. Dress rinsing typically includes spraying a picked carcass with water, typically at a temperature of about 5° C. to about 30° C. To increase contact with the carcass, the antimicrobial compositions in the spray water can be applied at higher pressures, flow rates, temperatures, or with agitation energy. Dress rinsing is typically accomplished with a washing apparatus such as a wash or spray cabinet with stationary or moving spray nozzles. Alternatively, a "flood"-rinsing or liquid submersion washing apparatus may be used immediately after picking. Any of these application methods may be used to apply antimicrobial compositions according to the method of the invention. For example, dress rinsing can be accomplished employing at least one peroxyacid, peroxygen, peracetic acid and/or hydrogen peroxide compound injected into water at a pH of from about 0.5 to about 3.5. In one aspect, dress rinsing may comprise applying about 90 ppm of antimicrobial composition comprising a mixture of peroxyacetic acid or hydrogen peroxide at 1 ppm to about 1000 ppm.

Dress rinsing is typically a final washing step before dismembering the poultry. Dismembering can include removing the head, the feet, eviscerating, and removing the neck, in any order commonly employed in poultry processing. The dismembered and eviscerated poultry can then be subjected to a washing step known as inside-outside bird washing (IOBW). Inside-outside bird washing washes the interior (body cavity) and exterior of the bird. Inside-outside bird washing typically includes rinsing the interior and exterior surfaces of the carcass with streams or floods of water, typically at a temperature of about 5° C. to about 30° C.

Antimicrobial spray and/or dip and/or cavity flood typically follows IOBW. Some processors refer to this as On-Line Reprocessing (OLR). Additional decontamination may be performed by antimicrobial spray rinsing, sanitizing rinsing, and/or finishing rinsing, which may include spraying the interior and exterior surfaces of the carcass with water, generally at a temperature of about 5° C. to about 30° C. Application may be performed using spray nozzles at high pressure, flow rate, and/or temperature. A spray cabinet with spray nozzles can create a mist, vapor, or spray that contacts the carcass surfaces.

After spray rinsing, the bird may undergo further processing by chilling, which may be performed by submersion chilling or air chilling. Submersion chilling typically comprises completely submersing the meat/poultry in water or slush, generally at a temperature of less than about 5° C. for a period of time sufficient to bring the temperature of the carcass at or below 5° C. The inventors have found that application of the invention at OLR and post-chill, with proper use of overflows, is sufficient to lower contamination below currently accepted levels.

An especially effective method for washing poultry employs a pressure spray of an antimicrobial composition formed by the method of the invention. During application of the spray solution on the poultry product, the surface of the poultry product can be moved with mechanical action, preferably agitated, rubbed, brushed, etc. Agitation may be by physical scrubbing of the poultry product, through the action of the spray solution under pressure, through sonication, or by other methods. Agitation increases the efficacy of the spray solution in killing micro-organisms, perhaps due to better exposure of the solution into the crevasses or small colonies containing the micro-organisms.

Application of the material by spray can be accomplished using a manual spray wand application, an automatic spray of poultry product moving along a production line using multiple spray heads to ensure complete contact or other spray means. One preferred spray application involves the use of a spray cabinet, which, in the method of the invention, may comprise an endpoint that is fluidly connected to the aqueous stream comprising the antimicrobial composition. The spray cabinet substantially confines the antimicrobial composition within the parameter of the cabinet. The production line moves the poultry product through the entryway into the spray cabinet in which the poultry product is dipped on all its exterior and interior surfaces come into direct contact with the antimicrobial composition. After a complete coverage of the material and drainage of the material from the poultry product within the cabinet, the poultry product can then exit the spray cabinet in a fully treated form. The spray pattern can be virtually any useful spray pattern.

During processing of a poultry product, the poultry product can be immersed into a dip tank containing a quantity of the antimicrobial solution. The washing solution is preferably agitated to increase the efficacy of the solution and the speed in which the solution reduces micro-organisms accompanying to the poultry product. It is preferable that the poultry product be immersed into a dip tank or finishing chiller at the final stage of the cooling process. However, a dip/immersion can be obtained by conventional methods, including ultrasonics, aeration by bubbling air through the solution, by mechanical methods, such as strainers, paddles, brushes, pump driven liquid jets, or by combinations of these methods. These poultry products can be immersed in a dip process of the antimicrobial solution before the poultry product starts the cooling process.

Washing poultry can employ a large volume of water, or another carrier. Poultry wash water can be used more than once (recycled), provided the water can be treated so that it does not transfer undesirable microbes to the poultry being washed with the recycled wash water. One way to prevent the transfer of such undesirable microbes, is to reduce the microbial burden of the recycled wash water by adding a mixture of the microbial composition. For example, if the fluid to be recycled is water-based and lacking any microbial composition, a mixed microbial composition can be added to result in an effective antimicrobial concentration in the fluid to be recycled. Alternatively, if the fluid to be recycled already includes or has included the microbial composition, a mixed microbial composition can be added to increase any concentration of the microbial composition to an effective antimicrobial level. It may be that the microbial composition in the solution to be recycled has been totally depleted, in which case more of the mixed microbial composition is added.

In some circumstances, the water to be recycled includes a substantial burden of organic matter or microbes. If this is the case, the water may be unsuitable for recycling. However, if the water is to be recycled, the operator adds a sufficient quantity of the mixed microbial composition to provide an effective antimicrobial amount of the microbial composition after a certain amount is consumed by the organic burden or microbes already present. Then, the recycled fluid can be used with antimicrobial effect. Routine testing can be employed for determining levels of the microbial composition, or of organic burden.

In each case, the method of recycling the poultry wash water includes recovering the poultry wash water, adding microbial composition, and reusing the poultry wash water for washing poultry, for example, as described above. The poultry wash water can be recovered from steps in poultry processing including submersion scalding, dress rinsing, inside-outside bird washing, spray rinsing, and submersion chilling. Methods of recovering wash water from these steps are well-known to those skilled in the poultry washing and/or processing arts. The wash water can also be strained, filtered, diluted, or otherwise cleaned or processed during recycling.

A method of application consisting of suppressing the pH of the carrier (i.e. the aqueous stream) prior to the injection of a peroxy chemical can be applied as an effective pathogen intervention system during the processing of red meat derived from bovine, porcine or ovine sources. It is equally as effective as an anti-microbial intervention in the processing or dressing of muscle tissue rendered from wild game and exotics.

The method can be effectively utilized as a anti-microbial intervention system for processing the whole carcasses (hide on and hide off), primal, sub-primals, organs, variety meats and value added products at any step post-knock, stunning or slaughter of the animal. Application may be achieved through a series of multiple steps and additions, not excluding combinations of the following: high pressure and low pressure cabinet washing, rinsing, sprays, chilling, or scalding to effectively reduce the extent of surface spoilage/decay-causing bacteria, and pathogenic bacteria.

In red meat decontamination, for example, post kill, the carcass typically passes through a series or a single large spray cabinet with a combination of high pressure and low pressure washes, followed by a rinse. It is commonplace for the first wash in incorporate a degree of alkalinity (caustic) with or without a surfactant to assist in the general softening and removal of dirt, debris and feces from the outer surface of the animal. Immediately following this typically high pressure wash, is a low pressure rinse that can employ an oxidizer (bleach, sodium or calcium hypochlorite, or one of several organic acids). Following the rinse the animal is stuck and blood drained. The hide is then removed either with the aid of a side or down puller. Once the hide is removed, the carcass typically passes through another low pressure spray cabinet using either an oxidizer or organic acid wash. The carcass is then cut into consecutively small sections (i.e. primals, then sub-primals), these sections passing through smaller spray cabinets that typically employ a low volume of a anti-microbial intervention chemistry. Similar spray cabinets are utilized for washing heads and organs, designed to remove blood and excess tissue, while applying a antimicrobial intervention methodology.

The present invention may be better understood with reference to the following non-limiting examples.

EXAMPLES

Broiler chickens were processed using a dip procedure, fully immersing the birds in an antimicrobial composition produced by the method of the invention. After approximately ten (10) seconds of immersion, individual birds were removed from the antimicrobial composition, placed in a sterile bag containing 400 milliliters of sterile Butterfield's Solution, and rinsed. An aliquot of the rinse solution was then plated by an independent microbiology laboratory to detect presence or absence of *Salmonella* sp. Results were reported as positive or negative. A total of 90 birds were collected, and results are shown in Table 1.

TABLE 1

|  | Control | 99 ppm PAA* | STACKED* |
|---|---|---|---|
| No. of samples | 20 | 40 | 30 |
| No. of positives | 8 | 5 | 0 |
| No. of negatives | 12 | 35 | 30 |
| % positives | 40.0 | 12.5 | 0.0 |

*"99 ppm PAA" represents a standard solution containing peroxyacetic acid at 99 ppm; "STACKED" represents an antimicrobial composition at a pH of from about 1.8 to about 2.0, produced by the method of the invention, the composition comprising PAA and 0.6% SYNTRx ® 3200 (Synergy Technologies), a highly buffered acid blend.

In a second round of testing, the STACKED composition, comprising water titrated to pH 1.8-2.0 (using SYNTRx® 3200 at 0.6%) and PM at 99 ppm, was compared to a composition comprising 400 ppm PM. Results are shown in Table 2.

TABLE 2

|  | Control | 400 ppm PAA | STACKED |
|---|---|---|---|
| No. of samples | 18 | 28 | 110 |
| No. of positives | 14 | 9 | 5 |
| No. of negatives | 4 | 19 | 105 |
| % positives | 77.8 | 32.1 | 4.5 |

Red Meat Efficacy Tests:

The inventors refer to the system for admixing and applying antimicrobial compositions according to the method of the invention as a "stacked" system. One the significant advantages of the "stacked" system is that it allows a meat processor, fabricator or converter to utilize lower use concentrations of peroxy compounds (e.g., peroxyacetic acid or PM), potentially making such programs more cost effective, while at the same time reducing associated acetic acid odors which are typically encountered.

In the inventors' tests they utilized Synergize P22, a concentrated version of PM which provides essentially 46% more active ingredient per gallon than competitive products that are currently available. A mixed inoculum isolate from bovine manure at an applied concentration of $2.7 \times 10^6$ (aerobic plate count or APC) was used. In addition, further microbial testing utilizing selective media confirmed that the inoculum contained a significant population of both coliform and Enterobacteriaceae. These were assumed to be representative of *E. coli* and *Salmonella* sp. The "stacked" approach was performed by injecting an approved organic (SYNTRx 3300—a highly buffered citric acid blend) or mineral acid to reach the targeted pH range, followed by the specified treatment concentration of the peroxy compound (in this case Synergize P22).

Results of this round of testing indicated a 0.5-1.0 log improvement in reductions over the industry practice of a standalone PM treatment. Observations were made within 30 minutes after the application of the intervention solution, after 4-hours with the treated beef stored at 40° F. and after 24-hours of storage. See Table 3 below.

TABLE 3

| Treatment | T = 0 | | T = 4 | | T = 24 | |
|---|---|---|---|---|---|---|
| | Log Reduction | % Reduction | Log Reduction | % Reduction | Log Reduction | % Reduction |
| Control | 0.1397 | 27.5 | 0.1008 | 20.71 | −0.0525 | * |
| #5 | 2.8672 | 99.86 | 2.5141 | 99.69 | 2.5129 | 99.69 |
| #6 | 2.8234 | 99.85 | 2.0929 | 99.19 | 2.1658 | 99.32 |
| #7 | 2.8123 | 99.42 | 2.5088 | 99.69 | 2.7016 | 99.80 |
| #8 | 2.5448 | 99.71 | 2.1942 | 99.36 | 2.8654 | 99.86 |
| #11 | 2.1924 | 99.36 | 1.9937 | 98.99 | 1.8719 | 98.66 |

Control = Water
5 = Synergize P22 (208 ppm PAA) + SYNTRx pH 1.2
6 = Synergize P22 (216 ppm PAA)
7 = Synergize P22 (216 ppm PAA) + SYNTRx pH 1.5
8 = Synergize P22 (220 ppm PAA) = SYNTRx pH 1.2 (120° F.)
11 = 15% PAA (220 ppm PAA)

While 200 ppm of PM yielded approximately 2 log reduction, or better than 98% reduction, in 4 hours, the "stacked" treatment provided a 2.5 log reduction, or 99.7% reduction (with the solution applied at ambient temperature).

What is claimed is:

1. A method of decontaminating food products comprising the steps of:
   (a) establishing an aqueous flowing stream;
   (b) introducing at least one strong acid into the aqueous flowing wherein the at least one strong acid is selected from a group consisting of hydrochloric acid, sulfuric acid and phosphoric acid;
   (c) providing a peroxyacetic acid (PAA);
   (d) admixing the peroxyacetic acid with the aqueous flowing stream separately from the at least one strong acid to provide an antimicrobial composition, wherein the concentration of said at least one strong acid ranges from about 5 to about 35 percent and the concentration of said peroxyacetic acid ranges from 1 ppm to about 1000 ppm of the antimicrobial composition, wherein the pH of the antimicrobial composition is from about 0.5 to about 3.5; and
   (e) applying the antimicrobial composition directly to the food product selected from the group consisting of poultry, meat, fish, fruit, and vegetables.

2. The method of claim 1, wherein the antimicrobial composition is directed to at least one endpoint selected from the group consisting of a mist, a spray, a dip, a deluge, a flume, an electrostatic application, and atomization, for application of the antimicrobial composition to the food product.

3. The method of claim 1, wherein the at least one strong acid comprises at least one buffered acid.

4. The method of claim 1, wherein the peroxyacetic acid comprises up to 1000 ppm for poultry.

5. The method of claim 1, wherein the peroxyacetic acid comprises up to 230 ppm for red meat.

6. The method of claim 1, wherein the peroxyacetic acid comprises from 1 ppm to about 1000 ppm for red meat.

7. The method of claim 3 where the buffered acid is a safe acid.

8. The method of claim 1 wherein the peroxyacetic acid is added to the aqueous stream before the addition of the at least one strong acid.

9. The method of claim 3, wherein the at least one buffered acid comprises hydrochloric acid (HCl).

10. The method of claim 3, wherein the at least one buffered acid comprises sulfuric acid ($H_2SO_4$).

11. The method of claim 3, wherein the at least one buffered acid comprises phosphoric acid ($H_3PO_4$).

12. A method of decontaminating a poultry product, comprising the steps of:
   (a) establishing an aqueous flowing stream;
   (b) introducing at least one strong acid into the aqueous flowing stream, wherein the at least one strong acid is selected from a group consisting of hydrochloric acid, sulfuric acid, and phosphoric acid;
   (c) providing a peroxyacetic acid;
   (d) admixing the peroxyacetic acid with the aqueous flowing stream separately from the at least one strong acid to provide an antimicrobial composition, wherein the concentration of said at least one strong acid is from about 5 to about 35 percent of the composition, wherein the pH of the composition is from about 0.5 to about 3.5, and wherein the peroxyacetic acid is less than 100 ppm; and
   (e) applying the composition directly to the poultry product on at least one endpoint selected from the group consisting of a mist, a spray, a dip, a deluge, a flume, an electrostatic application, and atomization.

13. The method of claim 12, wherein the at least one strong acid further comprises at least one buffered acid selected from a group consisting of hydrochloric acid, sulfuric acid, and phosphoric acid.

14. A method of decontaminating a red meat product, comprising the steps of:
   (a) establishing an aqueous flowing stream;
   (b) introducing at least one strong acid into the aqueous flowing stream, wherein the at least one strong acid is selected from a group consisting of hydrochloric acid, sulfuric acid, and phosphoric acid;
   (c) providing a peroxyacetic acid;
   (d) admixing the peroxyacetic acid with the aqueous flowing stream separately from the at least one strong acid to provide an antimicrobial composition, wherein the concentration of said at least one strong acid is from about 5 to about 35 percent of the composition, wherein the pH of the composition is from about 0.5 to about 3.5, and wherein the concentration of the peroxyacetic acid ranges from 1 ppm to about 1000 ppm; and
   (e) applying the composition directly to the red meat product on at least one endpoint selected from the group consisting of a mist, a spray, a dip, a deluge, a flume, an electrostatic application, and atomization.

15. The method of claim 14, wherein the at least one strong acid further comprises at least one buffered acid selected from a group consisting of hydrochloric acid, sulfuric acid, and phosphoric acid.

* * * * *